United States Patent [19]

Goldenberg

[11] Patent Number: 5,632,968
[45] Date of Patent: May 27, 1997

[54] DETECTION OF CARDIOVASCULAR LESIONS

[75] Inventor: David M. Goldenberg, Short Hills, N.J.

[73] Assignee: Immunomedics, Inc., Morris Plains, N.J.

[21] Appl. No.: 338,100

[22] Filed: Nov. 9, 1994

Related U.S. Application Data

[63] Continuation of Ser. No. 694,977, May 6, 1991, Pat. No. 5,364,612.

[51] Int. Cl.$^6$ .......................... A61K 51/10; A61B 5/055
[52] U.S. Cl. ................................ 424/1.49; 424/9.34
[58] Field of Search .......................... 424/1.49, 1.53, 424/9.34, 179.1, 180.1, 182.1

[56] References Cited

U.S. PATENT DOCUMENTS

| | | | |
|---|---|---|---|
| 4,364,936 | 12/1982 | Kung et al. | 424/85 |
| 4,624,846 | 11/1986 | Goldenberg | 424/1.1 |
| 4,634,586 | 1/1987 | Goodwin et al. | 424/1.1 |
| 4,698,420 | 10/1987 | Urnovitz | 530/387 |
| 4,767,843 | 8/1988 | Yazaki et al. | 530/387 |
| 4,783,330 | 11/1988 | Furie et al. | 424/1.1 |
| 4,820,505 | 4/1989 | Ginsberg et al. | 424/9 |
| 4,859,450 | 8/1989 | Khaw et al. | 424/9 |
| 4,863,729 | 9/1989 | Zuckerkandl | 424/85.8 |
| 4,868,109 | 9/1989 | Lansdorp | 435/28 |
| 4,916,070 | 4/1990 | Matsueda et al. | 435/172.2 |
| 4,925,648 | 5/1990 | Hansen et al. | 424/1.1 |
| 4,926,869 | 5/1990 | Rubin et al. | 128/654 |
| 4,986,979 | 1/1991 | Morgan, Jr. et al. | 424/1.1 |
| 4,990,326 | 2/1991 | Noujaim et al. | 424/9 |
| 5,026,537 | 6/1991 | Daddona et al. | 424/1.1 |
| 5,134,071 | 7/1992 | Gaetjens | 435/188 |
| 5,185,433 | 2/1993 | Dean et al. | 530/391.1 |
| 5,216,130 | 6/1993 | Line et al. | 530/362 |
| 5,225,181 | 7/1993 | Srivastava et al. | 424/1.1 |
| 5,256,395 | 10/1993 | Barbet et al. | 424/1.1 X |
| 5,277,894 | 1/1994 | Strauss et al. | 424/1.49 |
| 5,364,612 | 11/1994 | Goldenberg | 424/1.53 |
| 5,376,356 | 12/1994 | Morgan, Jr. | 424/1.41 |
| 5,439,665 | 8/1995 | Hansen et al. | 424/1.49 |
| 5,443,953 | 8/1995 | Hansen et al. | 424/1.49 |
| 5,503,982 | 4/1996 | Hendricks et al. | 435/7.21 |
| 5,541,296 | 7/1996 | Berman et al. | 530/388.22 |

FOREIGN PATENT DOCUMENTS

| | | |
|---|---|---|
| 0241907 | 10/1987 | European Pat. Off. . |
| 90/05544 | 5/1990 | WIPO . |

OTHER PUBLICATIONS

Goldberg et al., *Biochimica et Biophysica Acta*, vol. 959, pp. 220–228, 1988.

Rabinov et al, "Roentgen Diagnosis Of Venous Thrombosis In The Leg", *Phlebothrombosis Symposium*, 104:134–144, (1972).

Lensing et al, "Detection Of Deep–Vein Thrombosis By Real–Time B–Mode Ultrasonography", *The New England Journal of Medicine*, 320(6):342–345 (1989).

Colman et al, "Basic Principles And Clinical Practice", *Hemostasis And Thrombosis*, pp. 1123–1135, (1982).

Knight, "Radiopharmaceuticals For Thrombus Detection", *Nucl. Med.*, 20:52–67, (1990).

Koblik et al, "Current Status Of Immunoscintigraphy In The Detection Of Thrombosis And Thromboembolism", *Nucl. Med.*, 19:221–237, (1989).

Oster et al, "Thrombus Radioimmunoscintigraphy: An Approach Using Monoclonal Antiplatelet Antibody", *Proc. Natl. Acad. Sci. USA*, 82:3465–3468, (1985).

Seabold et al, "Pitfalls In Establishing The Diagnosis Of Deep Venous Thrombophlebitis By Indium–111 Platelet Scintigraphy", *J. Nucl. Med.*, 29:1169–1180, (1988).

Alavi et al, "Detection Of Venous Thrombosis With In–111 Labeled Antifibrin (59D8) Antibody Imaging", *J. Nucl. Med.*, 29:825, (1988).

Knight et al, "Fragment $E_1$ Labeled With I–123 In The Detection of Venous Thrombosis", *Radiology*, 156:509–514, (1985).

Khaw et al, "Acute Myocardial Infarct Imaging With Indium–111–Labeled Monoclonal Antimyosin Fab", *J. Nucl. Med.*, 28:1671–1678, (1987).

Johnson et al, "Antimyosin Imaging In Acute Transmural Myocardial Infarctions: Results Of A Multicenter Clinical Trial", *J. Am. Coll. Cardiol.*, 13:27–35, (1989).

Frame et al, "Early Membrane Damage During Coronary Reperfusion In Dogs", *J. Clin. Invest.*, 72:535–544, (1983).

Johnson et al, "The Role Of Antimyosin Antibodies In Acute Myocardial Infarction", *Semin. Nucl. Med.*, 19:238–246, (1989).

*Primary Examiner*—Ralph Gitomer
*Assistant Examiner*—Lara E. Chapman
*Attorney, Agent, or Firm*—Foley & Lardner

[57] ABSTRACT

This invention relates to reagents and methods for detecting and imaging cardiovascular lesions such as atherosclerotic plaques, vascular clots including thrombi and emboli, myocardial infarction, and other organ infarcts. Monospecific antibody imaging agent conjugates specific for one type of leukocyte, as well as multispecific antibody imaging agent conjugates specific for at least one type of leukocyte and for antigens associated with fibrin, myosin or platelets, are used in the present invention. Multispecific antibody imaging agent conjugates specific for at least two different antigens selected from the group consisting of fibrin-, myosin- and platelet associated antigens are also provided.

8 Claims, No Drawings

DETECTION OF CARDIOVASCULAR LESIONS

This application is a continuation of application Ser. No. 07/694,977, filed May 6, 1991, now U.S. Pat. No. 5,364,612.

BACKGROUND OF THE INVENTION

This invention relates to reagents and methods for detecting and imaging cardiovascular lesions such as atherosclerotic plaques, vascular clots including thrombi and emboli, myocardial infarction, and other organ infarcts. Monospecific antibody-imaging agent conjugates specific for one type of leukocyte as well as multispecific antibody-imaging agent conjugates specific for at least one type of leukocyte and for antigens associated with fibrin, myosin or platelet cells are used in the present invention. Also used in the present invention are multispecific antibody-imaging agent conjugates specific for at least two different antigens selected from the group consisting of fibrin, myosin, or platelet associated antigens.

When there is an insult to vascular endothelium, circulating blood cells, particularly leukocytes, accumulate. Granulocytes tend to concentrate in the largest numbers, but monocytes and lymphocytes also accumulate to a lesser degree. These cells wander through the vascular endothelium to congregate in the areas of injury. The granulocytes survive in the extravascular space for up to about three days, after which the mononuclear cells, monocytes and lymphocytes, become the dominant population.

Two phases are associated with a vascular insult, a brief early increase in vascular permeability and a more prolonged second phase consisting of increased permeability, attachment of leukocytes, mainly granulocytes, to the vessel wall, diapedesis of predominately leukocytes through the vessel wall, accumulation of leukocytes in the injured area, leukocyte phagocytosis, leakage of fibrinogen and platelets from the vessel, fibrin deposition in the injured area, intravascular clotting with vessel destruction, macrophage engulfment of necrotic debris, migration of fibroblasts and formation of connective tissue, and the neovascularization by ingrowth of capillaries. Thus, the infiltration by leukocytes, particularly granulocytes, is a very early and significant event.

The well-developed atherosclerotic plaque is a result of the interplay of inflammatory and repair events, resulting in a lesion consisting of extracellular calcium salts, cholesterol crystals, glycosaminoglycans, and blood cells and plasma components. Endothelial permeability of arterial walls is induced in early stages of atherosclerosis, allowing the afflux of circulating macromolecules and blood cells, particularly leukocytes (and mainly granulocytes). Secondary changes may involve reduction in permeability of the arterial intima, and the later deposition of platelets and/or fibrin, proliferative, degenerative, necrotic, and repair processes that result in atheromatous lesions. Here again, an early component is the concentration and extravasation of leukocytes in the injured area.

With regard to clots, when vessels are injured, plugging may occur by the formation of fibrin, the aggregation of platelets, and combinations of both. During these events, leukocyte sticking and aggregation, independent of platelet aggregation, occurs. Very early, even before fibrin formation, extravasation of leukocytes takes place.

Deep vein thrombosis (DVT) and pulmonary embolism are very common in the general population, affecting 30% to 60% of otherwise healthy men and women, and up to 80% in high-risk patients. It has been estimated that as much as 20% of all hospital patients are affected with thromboembolic events. In the U.S. alone, it has been estimated that 2.5 million cases occur each year (Sherry, Semin. Nucl. Med. 7: 205–211, 1977).

The majority of commonly used nuclear medicine tests for deep vein thrombosis (DVT) involve nonspecific radiopharmaceuticals employed for radionuclide venography. Thus, there is a great need for a thrombosis-specific radiopharmaceutical for specific, sensitive, and rapid disclosure of thrombi by non-invasive external scintigraphy. Contrast venography, a common radiological method, has been the "gold standard" for DVT, but it has a high incidence of side effects which limit its repeated use (Rabinov and Paulin, Arch. Surg. 104: 134–144, 1972). Compression B-mode ultrasound is also of use for diagnosing the presence of thrombi in the legs, but this is region-limited and, again, not lesion-specific (Lensing et al., N. Engl. J. Med. 320: 342–345, 1989). Hence, radiopharmaceuticals are being sought to achieve simplicity, rapidity, and specificity for the detection and diagnosis of DVT.

Where the aforementioned agents may be useful for DVT, they may fail to disclose pulmonary emboli, which are life-threatening lesions. Different thrombi may require different agents. Venous thrombi consist primarily of polymers of fibrin with entrapped cells, alternating with layers of platelets, whereas arterial thrombi are made up primarily of aggregated platelets with less fibrin (Freiman, in: Coleman et al., eds, Hemostasis and Thrombosis—Basic Principles and Clinical Practice. New York, N.Y., Lippincott, 56: 766–780 (1982)). Thus, there exists a need to have a radiopharmaceutical that can bind to both arterial and venous deposits.

For the most part, the agents available appear to be restricted to either fibrin-directed or platelet-directed pharmaceuticals, as reviewed by Knight (Semin. Nucl. Med., 20: 52–67, 1990).

Fibrin-specific radiopharmaceuticals include radiolabeled fibrinogen, soluble fibrin, antifibrin antibodies and antibody fragments, fragment $E_1$ (a 60 kDa fragment of human fibrin made by controlled plasmin digestion of crosslinked fibrin), plasmin (an enzyme in the blood responsible for dissolution of fresh thrombi), plasminogen activators (e.g., urokinase, streptokinase and tissue plasminogen activator), heparin, and fibronectin (an adhesive plasma glycoprotein of 450 kDa).

Platelet-directed pharmaceuticals include radiolabeled platelets, antiplatelet antibodies and antibody fragments, anti-activated-platelets, and anti-activated-platelet factors, which have been reviewed by Knight (cited above), as well as by Koblik et al., Semin. Nucl. Med., 19: 221–237 1989), all of which are included herein by reference. Platelet imaging is most useful during the acute phase of thrombosis, when active platelet aggregation occurs, so that these platelet-based imaging methods have difficulty in disclosing clots that are older than 24–48 hours (Oster et al., Proc. Natl. Acad. Sci. USA, 82: 3465–3468, 1985). Another concern is that platelet imaging may be inhibited by concurrent heparin administration in the treatment of these patients (Seabold et al., J. Nucl. Med. 29: 1169–1180, 1988). Heparinization can also reduce the total number of lesions found with anti-fibrin antibodies (Alavi et al., J. Nuci. Med., 29: 825, 1988). In comparison to antifibrin antibodies, fragment $E_1$ that is radiolabeled appears to demonstrate clots earlier (Koblik et al., cited above). However, the fragment $E_1$ is difficult to isolate and prepare, and its binding to blood clots is transient (Knight et al, *Radiology*, 156: 509–514, 1985). A need therefore continues to exist for a preparation containing a combination of two or more of these clot imaging agents, each of which complements the other(s); e.g., an anti-fibrin antibody or antibody fragment or fragment $E_1$ and an anti-leukocyte antibody or antibody fragment and/or an anti-platelet or anti-activated-platelet antibody or antibody fragment, or an anti-fibrin antibody or antibody fragment and an anti-platelet or anti-activated platelet antibody or fragment; all appropriately labelled.

Inadequate blood and oxygen supply to the myocardium, inducing symptoms of myocardial ischemia or ischemic heart disease, are the usual events resulting from stenotic coronary atherosclerosis. Acute and total coronary artery occlusion results in severe ischemia and, consequently, myocardial infarction. Chronologically, in the first hour, subcellular changes of ischemic heart muscle manifest as mitochondrial granules, reduction of glycogen and respiratory enzymes. Thereafter, from about 1 to 6 hours, margination and clumping of nuclear chromatin, loss of nuclear and myofilament architecture, and infiltration with granulocytes, are observed. In the next phase, from about 6 to 12 hours, typical ischemic necrosis is seen. After 24 hours, severe histological changes are easily seen, leading to focal hemorrhage of different size and dilated capillaries by days 2–4.

The available tests for diagnosing, pinpointing, and determining the extent of myocardial infarction (MI), such as EKG, creatinine kinase (CK-MB) curves, ejection fraction, are all burdened with some limitations. Nuclear imaging methods using $^{99m}$Tc pyrophosphate or $^{201}$thallium (TI) have been developed to diagnose and quantify MI. In the last years, antibodies and antibody fragments against myosin have been used experimentally and clinically to demonstrate localization in myocardial cells irreversibly damaged by an ischemic insult (Khaw et al., *J. Nucl. Med.* 28: 1671–1678 1987); Johnson et al. *J. Am. Coll. Cardiol.* 13: 27–35, 1989). Uptake of myosin antibody is claimed to be specific for cell death (Framie et al., *J. Clin. Invest.* 72: 535–544, 1983), and it was found in the clinical studies (cited above) that at least 24 hours are needed before imaging was revealing. Thus, at least 2 or more days were required after the ischemic insult before anti-myosin imaging would work successfully because sufficient cell death must first ensue to result in sufficient antigen sites available for the anti-myosin antibody binding. Thus, there is a need for an agent or combination of agents that will be diagnostic before the occurrence of extensive cell death and myocardial damage and can also combine the attributes of an anti-myosin antibody with a leukocyte-imaging agent. Therefore, for early infarction or even atheromatous plaques, an anti-leukocyte antibody suffices for imaging, such as within the first few hours after the ischemic insult.

OBJECTS OF THE INVENTION

One object of the present invention is to provide an antibody, Ab fragment, or Ab subfragment-imaging agent conjugate which binds to one type of leukocyte for targeting and early imaging of cardiovascular lesion, such as atherosclerosis, vascular clots including thrombi and emboli, and myocardial infarcts and other organ infarcts.

Another object of the present invention is to provide a multispecific antibody, Ab fragment, or Ab subfragment composite-imaging agent conjugate which selectively binds to at least one type of leukocyte and selectively binds to at least one antigen associated with fibrin, myosin, or platelets for targeting and early imaging of cardiovascular lesions with an enhanced target-to-background ratio.

Another object of the present invention is to provide a multispecific antibody, Ab fragment, or Ab subfragment composite-imaging agent conjugate which selectively binds to at least two different antigens selected from the group consisting of fibrin-, myosin- or platelet-associated antigens for targeting and early imaging of cardiovascular lesions with an enhanced target-to-background ratio.

Another object of the present invention is to provide a method for targeting monospecific or multispecific antibody-agent conjugates to cardiovascular lesions with higher efficiency and an enhanced target to background ratio.

Still another object of the invention is to provide reagents and methods for more efficient detection of cardiovascular lesions.

Yet another object of the invention is to provide reagents and methods for earlier detection of cardiovascular lesions.

Other objects of the present invention will become more apparent to those of ordinary skill in the art in light of the following discussion.

SUMMARY OF THE INVENTION

These and other objects of the present invention are achieved by providing a monospecific antibody-imaging agent conjugate for targeting and imaging cardiovascular lesions comprising a monospecific antibody or antibody fragment conjugated to at least one imaging agent, wherein said antibody or antibody fragment specifically binds to one type of leukocyte.

Another object of the present invention is achieved by providing a multispecific antibody-agent conjugate for targeting and imaging cardiovascular lesions comprising an immunoreactive multispecific composite of at least two different substantially monospecific antibodies or antibody fragments, conjugated to at least one imaging agent, wherein at least one of said antibodies or antibody fragments specifically binds to one type of leukocyte and at least one of said antibody or antibody fragments binds to an antigen associated with fibrin, myosin or platelets.

Another object of the present invention is achieved by providing a multispecific antibody-agent conjugate for targeting and imaging cardiovascular lesions comprising an immunoreactive multispecific composite of at least two different substantially monospecific antibodies or antibody fragments, conjugated to at least one imaging agent, wherein at least two of said antibodies or antibody fragments specifically bind to at least two different antigens selected from the group consisting of fibrin-, myosin-, or platelet-associated antigens.

Another object of the present invention is achieved by providing a multispecific antibody-agent conjugate for targeting and imaging various cardiovascular lesions comprising an immunoreactive multispecific composite of at least two different substantially monospecific antibodies or antibody fragments, conjugated to at least one imaging agent, wherein at least one of said antibodies or antibody fragments specifically bind to one type of leukocyte and at least one of said antibody or antibody fragments binds to an antigen associated with fibrin, myosin or platelets.

Another object of the present invention is achieved by providing a multispecific antibody-agent conjugate for targeting and imaging various cardiovascular lesions comprising an immunoreactive multispecific composite of at least two different substantially monospecific antibodies or antibody fragments, conjugated to at least one imaging agent, wherein at least two of said antibodies or antibody fragments specifically bind to two different antigens selected from the group consisting of fibrin-, myosin- or platelet-associated antigens.

The invention also provides a method for imaging various cardiovascular lesions which comprises injecting a mammal parenterally with an effective amount for targeting and imaging of the foregoing monospecific or polyspecific antibody-agent conjugates.

The invention further provides a method for early diagnosis of cardiovascular lesions comprising injecting a mammal parenterally with an effective amount for targeting of the foregoing monospecific or multispecific antibody agent conjugates.

In addition, the present invention provides sterile injectable preparations and kits for use in practicing the foregoing method.

DETAILED DESCRIPTION OF THE INVENTION

The present invention provides an improvement over the prior art imaging methods for cardiovascular lesions, such as atherosclerotic plaques, vascular clots including thrombi and emboli, myocardial infarcts, and other organ infarcts because it enables sensitive targeting of the diagnostic agent to the pathological site very early after the injury occurs, thus permitting better diagnosis and earlier implementation of therapy.

A preferred improvement is the use of multispecific antibody composites. The multispecific targeting antibody composite comprises at least two different substantially monospecific antibodies or antibody fragments, wherein at least one of the antibodies or antibody fragments specifically binds to one type of leukocyte and at least one of the antibodies or antibody fragments specifically binds to an antigen associated with fibrin, myosin or platelets. Thus, at least one antigen binding site on the composite will bind to a first leukocyte cell type while at least a second antigen binding site on the same targeting composite will bind to an antigen associated with fibrin, myosin or platelets. The types of leukocytes include granulocytes, monocytes, B-lymphocytes and T-lymphocytes, which are involved in the development of cardiovascular lesions.

The immunological profile of the substantially monospecific, preferably monoclonal, antibodies used to make the antibody composites of the present invention can be adjusted to ensure optimal binding to the cardiovascular lesions and minimal binding to nontarget sites. A mixture of antibodies, antibody fragments, or subfragments, with different specificities, i.e., leukocytes, and antigens associated with fibrin, myosin and platelets can improve the percentage of injected dose reaching the target site if the right proportion of specificities is used. The imaging agent component of the antibody-agent conjugate is thereby localized at the target site with higher efficiency and an enhanced target-to-background ratio. Since leukocyte infiltration is a very early event in cardiovascular lesions, this method allows very early recognition of the occurrence of atherosclerosis, ischemic heart disease, clots and emboli, even sooner than using other currently known antibody radioconjugates or diagnostic agents.

The immunoreactive conjugates according to the invention can comprise monospecific, bispecific, trispecific or, more generally, multispecific antibody/fragment/ subfragment, Fv or single chain binding proteins, conjugated to an imaging radioisotope, fluorescent agent, computed tomography contrast agent, or paramagnetic species (magnetic resonance contrast agent). The antibody component of the conjugate can be made with whole antibodies, antibody fragments, subfragments (Fv or smaller binding units), of a single mammalian species or of a genetically-engineered combination of species (such as a combination of human and rodent, in so-called humanized or chimerized antibodies). Antibodies can be whole immunoglobulin of any class, e.g., IgG, IgM, IgA, IgD, IgE, chimeric or hybrid antibodies with dual or multiple antigen or epitope specificities, or fragments, e.g., F(ab')$_2$, F(ab)$_2$, Fab, Fab', Fv, and the like, including hybrid fragments, and additionally includes any immunoglobulin or any natural, synthetic or genetically engineered protein, e.g., a single chain antibody fragment that acts like an antibody by binding to a specific antigen to form a complex.

Monoclonal antibodies are suitable for use in the present invention, and are preferred because of their high specificities. They are readily prepared by what are now generally considered conventional procedures for immunization of mammals with an immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present invention. Use of purely human monoclonal antibodies is also preferred, since this would decrease immunogenicity of the reagent to the patient.

The present invention also envisions the use of antigen-specific fragments to create the multispecific antibody-agent conjugate. Antibody fragments can be made by pepsin or papain digestion of whole immunoglobulins by conventional methods. It is known that antibody fragments may be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively an enzymatic cleavage using pepsin produces two monovalent Fab fragments and an Fc fragment directly. These methods are described, inter alia, by Goldenberg, in U.S. Pat. Nos. 4,036,945 and 4,331, 647 and references contained therein, which patents are incorporated herein in their entireties by reference, and in Nisonoff et al, Arch. Biochem. Biophys., 89,230 (1960); Porter, Biochem. J., 73, 119 (1959); and Edelman et al, in "Methods in Immunology and Immunochemistry", Vol. 1, 422 (Acad. Press, 1967), and are conventional in the art.

Other methods of cleaving antibodies, such as separation of heavy chains to form monovalent light-heavy chain fragments, further cleavage of fragments, or other enzymatic, chemical or genetic techniques may also be used, so long as the fragments retain specificity to the antigen against which their parent antibodies are raised.

Antibodies to leukocyte antigens may be made by inoculating a host with leukocytes from the patient species. For instance, antibodies for use in humans may be made by immunizing mice or other mammalian species with human leukocytes. Anti-human leukocyte serum may be collected from the host and affinity purified to provide polyclonal antibody for making the composite. Alternatively, splenocytes may be taken from the immunized host and fused with a suitable tumor cell line using somatic cell hybridization techniques to produce hybridomas that produce anti-leukocyte antibodies. These hybridomas may be isolated, subcloned and cultivated to produce monoclonal antibodies.

Monoclonal antibodies or fragments that recognize and bind to a leukocyte antigen are available commercially or may be made from somatic cell hybridization techniques described originally by Kohler, B. and Milstein, C., Nature (1975) 256: 495–497 and reviewed at length in Monoclonal Antibodies, Kennett, T. J., et al, eds, Plenum (1980). Commercially available monoclonal antibodies to leukocyte antigens are represented by: OKT anti-T cell monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2; G7Ell, W8E7, NKP15 and GO22 (Becton Dickinson); NEN9.4 (New England Nuclear); and FMC11 (Sera Labs).

The catalogue of Immunotech (Marseille, France, with worldwide distribution including Pel Freeze, Brown Deer, Wis., USA) lists commercially available monoclonal anti-leukocyte antibodies, many of which are suitable for preparing composites or therapy reagents according to the present invention. These include antibodies that specifically bind to T-cells, activated T-cells, B-cells, monocytes and granulocytes, including subpopulations thereof. Certain of the antibodies bind to antigens common to more than one type of leukocyte, e.g., monocytes and granulocytes, B-cells and granulocytes, T-cells and B-cells, T-cells and granulocytes, T-cells and monocytes and granulocytes and B-cells, and the like. The antibodies produced and distributed by Immunotech are similar to other antibodies from clones available elsewhere.

Suitable anti-T-cell antibodies include antibodies which bind to the CD1, CD2, CD4, CD6, CD7 or CD8 antigens. Preferred anti-T-cell antibodies are those that bind to the CD3 antigen and the CD5 antigen. A preferred antibody that binds to both monocyte and granulocyte antigens is a monoclonal which binds in particular to the CDW14 antigen. Preferred antibodies that bind to B-cells include antibodies that bind to the CD19 or CD21 antigens. Antibodies that bind to activated T-cells include monoclonals that bind to the CD25 or CD26 antigens. The CD antigens are leukocyte determinants that define antibodies having particular leukocyte specificities. A pair of antibodies that bind to the same epitope on the same CD antigen will cross-block binding to the same type of leukocyte. Antibodies that bind specifically to the Ia (HLA-DR) histocompatibility antigen common to monocytes, B-lymphocytes and activated T-lymphocytes are classified as anti-HLA-DR Class II antibodies, and are of particular utility for certain applications.

The commercially available monoclonal antibodies to leukocyte antigens are typically of murine or rat origin and typically are IgGs or IgMs, although suitable antibodies for use in preparing conjugates according to the invention are not intended to be limited as regards species or Ig class. In general, antibodies can usually be raised to most antigens, using the many conventional techniques now well known in the art. Any antibody that binds to a leukocyte antigen which is found in sufficient concentration at a cardiovascular lesion in the body of a mammal can be used to make the targeting multispecific antibody composite for use in the present invention.

It is generally desirable to use antibodies having a relatively high immunoreactivity, i.e., a binding constant of at least about $10^5$ l/mole, preferably at least about $10^7$ l/mole, and high immunospecificity, i.e., at least about 40%, preferably at least about 60%, more preferably at least about 70–95% for leukocyte antigens.

It may be preferable for certain applications to use antibodies having a somewhat lower binding constant in the present invention. Antibodies with high binding constants are likely to bind tightly not only to leukocytes at the site of injury but also to leukocytes present in the circulatory system, the marrow or normal tissues. On the other hand, antibodies with a lower binding constant will tend to accrete mainly at concentrated leukocyte foci at the site of a lesion, by virtue of a type of mass action effect. This will reduce premature clearance and nontarget accretion of the imaging label.

A description of current antibodies against fibrin and platelet antigens is contained in Knight, Semin. Nucl. Med., 20: 52–67 (1990), which is incorporated herein by reference. Anti-myosin antibodies are described in Khaw et al., J. Clin. Invest, 58: 439–446, 1976; Khaw et al., Hybridoma, 3: 11–23 (1984), which are herein incorporated by reference.

Antibody composites for imaging can be prepared by a variety of conventional procedures, ranging from simple glutaraldehyde linkage to more elegant and specific linkages between functional groups. The antibodies and/or antibody fragments are preferably covalently bound to one another, directly or through a short or long linker moiety, through one or more functional groups on the antibody/fragment, e.g., amine, carboxyl, phenyl, thiol or hydroxyl groups. Various conventional linkers in addition to glutaraldehyde can be used, e.g., diisocyanates, diisothiocyanates, bis(hydroxysuccinimide) esters, carbodiimides, maleimide-hydroxysuccinimide esters and the like.

A simple, method is to mix the antibodies/fragments in the presence of glutaraldehyde to form the antibody composite. The initial Schiff base linkages can be stabilized, e.g., by borohydride reduction to secondary amines. This method is conventionally used to prepare other conjugates of proteins, e.g., peroxidase-antibody conjugates for immunohistochemical uses or for immunoassays. A diisothiocyanate or a carbodiimide can be used in place of glutaraldehyde as a non-site-specific linker.

Bispecific antibodies can be made by a variety of conventional methods, e.g., disulfide cleavage and reformation of mixtures of whole IgG or, preferably, F(ab')$_2$ fragments, fusions of more than one clone to form polyomas that produce immunoglobulins having more than one specificity, and by genetic engineering. The bispecific antibodies can bind to combinations of leukocytes and other cells or proteins associated with cardiovascular lesions such as fibrin, myosin, or platelets. Bispecific antibodies can also bind to two different antigens selected from the group consisting of fibrin-, myosin-, or platelet-associated antigens. Bispecific ("hybrid") antibody fragments have been prepared by oxidative linkage of F(ab') fragments resulting from reductive cleavage of different antibodies. A portion of these will contain fragments specific to both of the antigens to which the original antibodies were raised. This is advantageously carried out by mixing two different F(ab')$_2$ fragments produced by pepsin digestion of two different antibodies, reductive cleavage to form a mixture of Fab' fragments, followed by oxidative reformation of the disulfide linkages to produce a mixture of Fab'$_2$ fragments including hybrid fragments containing a F(ab') portion specific to each of the original antigens. Methods of preparing such hybrid antibody fragments are disclosed in Feteanu, "Labeled Antibodies in Biology and Medicine" pages 321–323 (McGraw-Hill Int. Bk. Co., New York et al, 1978);

Nisonoff et al, Arch Biochem. Biophys., 93, 470 (1961); and Hammerling et al, J. Exp. Med., 128, 1461 (1968); and in U.S. Pat. No. 4,331,647.

More selective linkage can be achieved by using a heterobifunctional linker such as a maleimide-hydroxysuccinimide ester. Reaction of the latter with an antibody/fragment will derivatize amine groups on the antibody/fragment, and the derivative can then be reacted with, e.g., an antibody Fab' fragment with free sulfhydryl groups (or a larger fragment or intact immunoglobulin with sulfhydryl groups appended thereto by, e.g., Traut's Reagent). Such a linker is less likely to crosslink groups in the same antibody and improves the selectivity of the linkage.

It is advantageous to link the antibodies/fragments at sites remote from the antigen binding sites. This can be accomplished by, e.g., linkage to cleaved interchain sulfhydryl groups, as noted above. Another method involves reacting an antibody whose carbohydrate portion has been oxidized with another antibody which has at least one free amine function. This results in an initial Schiff base (imine) linkage, which is preferably stabilized by reduction to a secondary amine, e.g., by borohydride reduction, to form the final composite. Such site-specific linkages are disclosed, for small molecules or polypeptides or for solid phase polymer supports, in U.S. Pat. No. 4,671,958, and for larger addends in U.S. Pat. No. 4,699,784.

Included among the various types of bispecific antibody composites of the present invention are the following, which are particularly useful for certain applications: a composite of antibodies/fragments specific to leukocytes and myosin for the detection of myocardial infarcts and atherosclerotic plaques. Thus, for general purpose MI imaging, a combined preparation of an anti-myosin antibody and an anti-leukocyte antibody is preferred. Preferred are Fab' or single-chain antibody forms, which would allow for very rapid targeting, by achieving a very high lesion-to-blood ratio, after injection. This improvement would then permit this diagnostic method to be used in the emergency room, when a patient is admitted with chest pain and other signs and symptoms of an MI. This early application is not currently possible with the use of anti-myosin antibodies alone (Johnson and Seldin, *Semin. Nucl. Med.* 19: 238–246, 1989).

Also included is a composite of antibodies/fragments specific to leukocytes and fibrin associated antigens for the detection of thrombi; a composite of antibodies/fragments specific to leukocytes and platelet associated antigens for the detection of thrombi; and a composite of antibodies/fragments specific to fibrin and platelet-associated antigens for the detection of thrombi and emboli.

The terms "multispecific antibody agent conjugate" and "multispecific composite" as used in the claims, also include bispecific antibody agent conjugates and bispecific composites, respectively.

Similar reactions can be used to bind a plurality of antibodies and/or antibody fragments, e.g., Fab or F(ab')$_2$ fragments, to one another to form multispecific composites. Bispecific composites can be linked to an antibody/fragment specific to a third, fourth or further leukocyte cell type or antigen associated with myosin, fibrin, or platelets using, e.g., a heterobifunctional maleimide-hydroxysuccinimide ester linker to derivatize an amine group, followed by reaction of the derivative with a fragment having a free sulfhydryl group, optionally introduced with a reagent such as 2-iminothiolane. Alternative linkage modes will be readily apparent to the ordinary skilled artisan based on the disclosures for bispecific composite formation, and will require only minor variation and adaptation of such methods.

Included among the various types of trispecific or multispecific antibody composites of the present invention is a composite of antibodies/fragments specific to leukocytes and antigens associated with fibrin and platelets for the detection of thrombi and pulmonary emboli. Other such multispecific composites will be readily apparent to the skilled artisan.

The monospecific antibody or antibody composite can be labeled with, or conjugated or adapted for conjugation to, a radioisotope for scintigraphic imaging or a magnetic resonance image enhancing agent, for use as a diagnostic imaging agent. Any conventional method of radiolabeling which is suitable for labeling proteins for in vivo use will be generally suitable for labeling the composite. This can be achieved by direct labeling with, e.g., a radioisotope of a halogen or a metal ion, using conventional techniques or more sophisticated methodologies, or by attaching a chelator for a radiometal or paramagnetic ion. Such chelators and their modes of attachment to antibodies are well known to the ordinary skilled artisan and are disclosed inter alia in, e.g., Childs et al., J. Nuc. Med., 26: 293 (1985); and in Goldenberg U.S. Pat. Nos. 4,331,647, 4,348,376, 4,361,544, 4,468,457, 4,444,744, and 4,624,846. Typical are derivatives of ethylenediaminetetraacetic acid (EDTA) and diethylenetriaminepentaacetic acid (DTPA). These typically have groups on the side chain by which the chelator can be attached to an antibody. Alternatively, carboxyl or amine groups on a chelator can be activated and then coupled to an antibody composite by well known methods. For example, deferoxamine, which is a chelator for Ga-67 has a free amine group that can be activated with a suitable linker to contain an activated carboxyl, isothiocyanate or like group, and then coupled to amines on an antibody composite.

The chelator may be bound to the antibody composite, directly or through a short or long chain linker moiety, through one or more functional groups on the antibody, e.g., amine, carboxyl, phenyl, thiol or hydroxyl groups. Various conventional linkers can be used, e.g., diisocyanates, diisothiocyanates, carbodiimides, bis-hydroxysuccinimide esters, maleimide-hydroxysuccinimide esters, glutaraldehyde and the like, preferably a selective sequential linker such as the anhydride-isothiocyanate linker disclosed in U.S. Pat. No. 4,680,338.

Labeling with either Iodine-131 (I-131) or Iodine-123 (I-123) is readily effected using an oxidative procedure wherein a mixture of radioactive potassium or sodium iodide and the antibody is treated with chloramine-T, e.g., as reported by Greenwood et al, Biochem. J., 89, 114 (1963) and modified by McConahey et al, Int. Arch. Allergy Appl. Immunol., 29, 185 (1969). This results in direct substitution of iodine atoms for hydrogen atoms on the antibody molecule, presumably on tyrosine residues, possibly also on tryptophan and even on phenylalanine residues, depending on the proportions of reagents and the reaction conditions. Alternatively, lactoperoxidase iodination may be used, as described by Feteanu, supra, page 303, and references cited therein.

Some more advanced methods of labeling are disclosed in pending applications U.S. Ser. Nos. 06/742,436 (filed Jun. 7, 1985), now U.S. Pat. No. 4,824,659, 07/084,544 (filed Aug. 12, 1987), now abandoned, and 07/176,421 (filed Apr. 1, 1988), now U.S. Pat. No. 5,061,641. The disclosures of all of the foregoing patents and applications are incorporated herein in their entireties by reference. A wide range of labeling techniques are disclosed in Feteanu, "Labeled Antibodies in Biology and Medicine", pages 214–309 (McGraw-Hill Int. Book Co., New York et al, 1978). The introduction of various metal radioisotopes may be accomplished according to the procedures of Wagner et al., J. Nucl. Med., 20,428 (1979); Sundberg et al, J. Med. Chem., 17, 1304 (1974); and Saha et al. J. Nucl. Med., 6, 542 (1976). The foregoing are merely illustrative of the many methods of radiolabeling proteins known to the art.

Examples of compounds useful for MRI image enhancement include paramagnetic ions, e.g., Gd(III), Eu(III), Dy(III), Pr(III), Pa(IV), Mn(II), Cr(III), Co(III), Fe(III), Cu(II), Ni(II), Ti(III) and V(IV) ions, or radicals, e.g., nitroxides, and these would be conjugated to a substrate bearing paramagnetic ion chelators or exposed chelating functional groups, e.g., SH, $NH_2$, COOH, for the ions, or linkers for the radical addends. The MRI enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in, e.g., Pykett, Scientific American, 246: 78 (1982); and Runge et al., Am. J. Radiol., 141: 1209 (1987).

It is well understood that many of the same methods for introducing metals, directly or in the form of chelates, into antibodies will be suitable for introduction of MRI agents into the antibody composites of the invention to form imaging agents for infectious lesions. MRI agents advantageously have a large number of paramagnetic ions or radicals for enhanced imaging. One method for introducing a plurality of such ions is to load a carrier polymer with chelates and link the carrier to the antibody composite, preferably site-specifically at a site remote from the antigen binding sites of the composite. This has the advantage that larger numbers of chelators can be attached to the antibody at fewer sites on the antibody itself, so that immunoreactivity is not as seriously compromised. Examples of polymers that are useful for loading the antibody with chelator include, e.g., polyols, polysaccharides, polypeptides and the like. See U.S. Pat. No. 4,699,784 (Shih et al) and U.S. Pat. No. 4,046,722 (Rowland). One type of polysaccharide is dextran. The chelator can be functionalized to contain reactive groups towards the dextran hydroxyls, e.g., anhydrides, isocyanates or isothiocyanates and the like. Alternatively, dextran can be derivatized in a number of ways, e.g., by conversion to an aminodextran. It will be appreciated that similar methods will be useful for loading a plurality of drug molecules on an antibody or antibody composite, as will be discussed more fully hereinafter.

The process for preparing an antibody conjugate with an aminodextran (AD) carrier normally starts with a dextran polymer, advantageously a dextran of average molecular weight (MW) of about 10,000–100,000, preferably about 10,000–40,000, and more preferably about 15,000. The dextran is then reacted with an oxidizing agent to effect a controlled oxidation of a portion of its carbohydrate rings to generate aldehyde groups. The oxidation is conveniently effected with glycolytic chemical reagents, e.g., $NaIO_4$, according to conventional procedures.

It is convenient to adjust the amount of oxidizing agent so that about 50–150, preferably 100 aldehyde groups are generated, for a dextran of MW of about 40,000, with about the same proportion of aldehyde groups for other MW dextrans. A larger number of aldehyde groups, and subsequent amine groups, is less advantageous because the polymer then behaves more like polylysine. A lower number results in less desirable loading of the chelator or boron addend, which may be disadvantageous.

The oxidized dextran is then reacted with a polyamine, preferably a diamine, and more preferably a mono- or poly-hydroxy diamine. Suitable amines include, e.g., ethylenediamine, propylenediamine or similar polymethylenediamines, diethylenetriamine or like polyamines, 1,3-diamino-2-hydroxypropane or other like hydroxylated diamines or polyamines, and the like. An excess of the amine relative to the aldehyde groups can be used, to insure substantially complete conversion of the aldehyde functions to Schiff base (imine) groups.

Reductive stabilization of the resultant intermediate is effected by reacting the Schiff base intermediate with a reducing agent, e.g., $NaBH_4$, $NaBH_3CN$, or the like. An excess of the reducing agent is used to assure substantially complete reduction of the imine groups to secondary amine groups, and reduction of any unreacted aldehyde groups to hydroxyl groups. The resultant adduct can be further purified by passage through a conventional sizing column to remove cross-linked dextrans. An estimate of the primary number of available amino groups on the AD can be effected by reaction of a weighed sample with trinitrobenzenesulfonic acid and correlation of the optical density at 420 nm with a standard. This method normally results in essentially complete conversion of the calculated number of aldehyde groups to primary amine groups on the AD.

Alternatively, the dextran can be derivatized by conventional methods for introducing amine functions, e.g., by reaction with cyanogen bromide, followed by reaction with a diamine. The AD should be reacted with a derivative of the particular drug or chelator, in an activated form, preferably a carboxyl-activated derivative, prepared by conventional means, e.g., using dicyclohexylcarbodiimide (DCC) or a water soluble variant thereof.

The scintigraphic imaging method of the invention is practiced by injecting a mammal, preferably a human, parenterally with an effective amount for scintigraphic imaging of the radiolabeled monospecific or multispecific antibody agent conjugate. By parenterally is meant, e.g. intravenously, intraarterially, intrathecally, interstitially or intracavitarily. For imaging cardiovascular lesions, intravenous or intraarterial administration is preferred. It is contemplated that a subject will receive a dosage of from about 1 mCi to 50 mCi of radiolabeled conjugate, the amount being a function of the particular radioisotope and mode of administration. For intravenous or arterial injection, the amounts are normally: about 2–10 mCi, preferably about 2–5 mCi, of I-131; about 5–10 mCi, preferably about 8 mCi, of I-123; about 10–40 mCi, preferably about 20 mCi of Tc-99m; about 2–5 mCi, preferably about 4 mCi of In-111 or Ga-67.

The radiolabeled monospecific or multispecific antibody-agent conjugate is conveniently provided as an injectable preparation for mammalian use, preferably a sterile injectable preparation for human use, for targeting a scintigraphic imaging agent to a cardiovascular lesion, preferably comprising: a sterile injectable solution containing an effective amount of the radiolabeled composite in a pharmaceutically acceptable sterile injection vehicle, preferably phosphate-buffered saline (PBS) at physiological pH and concentration. Other conventional pharmaceutically acceptable vehicles may be utilized as required for the site of parenteral administration.

A representative preparation to be parenterally administered in accordance with this invention will normally contain about 0.1 to 20 mg, preferably about 0.5 to 2.0 mg, of radiolabeled monospecific or polyspecific antibody-agent conjugate, in a sterile solution which advantageously also contains, e.g., about 10 mg of human serum albumin (1% USP: Parke-Davis) per milliliter of 0.04M phosphate buffer (pH 7.4 Bioware) containing 0.9% sodium chloride.

Once enough isotope has deposited at the target site, scanning is effected with either a conventional planar and/or SPECT gamma camera, or by use of a hand held gamma probe used externally or internally to localize the cardoivascular lesion. The scintigram is normally taken by a gamma imaging camera having one or more windows for detection of energies in the 50–500 KeV range. The target site can be any cardiovascular lesion present in a relatively concentrated focus. Detection of cardiovascular lesions will occur directly through reactivity of the monospecific or multispecific antibody-agent conjugate with the leukocytes and specific target antigens localized at the lesion at the time of parenteral administration as well as through entry of labeled leukocytes into the lesion.

Magnetic resonance imaging (MRI) is effected in an analogous method to scintigraphic imaging except that the imaging agents will contain MRI enhancing species rather than radioisotopes. It will be appreciated that the magnetic resonance phenomenon operates on a different principle from scintigraphy. Normally the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to increase both $T_1$, and $T_2$, the former resulting in greater contrast, while the latter results in lesser contrast. Accordingly the phenomenon is concentration-dependent, and there is normally an optimum concentration of a paramagnetic species for maximum efficacy. The optimum concentration will vary with the particular agent used, the locus of imaging, the mode of imaging, i.e., spin-echo, saturation-recovery, inversion-recovery and for various other strongly $T_1$ dependent or $T_2$ dependent imaging techniques, and the composition of the medium in which the agent is dissolved or suspended. These factors, and their relative importance are known in the art. See, e.g., Pykett, op.cit., and Runge et al., op.cit.

The MRI method of the invention is practiced by injecting a mammal, preferably a human, parenterally with an effective amount for magnetic resonance imaging of a conjugate according to the present invention comprising a monospecific or multispecific antibody composite and an MRI enhancing agent. It is contemplated that a subject will receive a dosage of labeled conjugate sufficient to enhance the MRI signal at the site of a lesion by at least about 20%, preferably 50–500%, the amount being a function of the particular paramagnetic species and the mode of administration.

Again, the labeled antibody or antibody composite is conveniently provided as an injectable preparation for mammalian use, preferably a sterile injectable preparation for human use, for targeting a MRI agent to a cardiovascular lesion, preferably comprising: a sterile injectable solution containing an effective amount of the labeled composite in a pharmaceutically acceptable sterile injection vehicle, preferably phosphate-buffered saline (PBS) at physiological pH and concentration. Other conventional pharmaceutically acceptable vehicles for parenteral administration may be utilized as required for the site of parenteral administration.

A representative preparation to be parenterally administered in accordance with this invention will normally contain about 0.1 to 20 mg, preferably about 5 mg, of labeled multispecific antibody-agent conjugate, in a sterile solution which advantageously also contains, e.g., about 10 mg of human serum albumin (1% USP: Parke-Davis) per milliliter of 0.04M phosphate buffer (pH 7.4 Bioware) containing 0.9% sodium chloride. Once enough of the MRI agent has deposited at the target site, scanning is effected with a conventional MRI camera to image the lesion.

In a preferred embodiment of this invention, the localization ratio of the primary labeled antibody-agent conjugate is enhanced through the use of a nonlabeled second antibody to scavenge non-targeted circulating conjugate and promote its clearance, as disclosed for related imaging agents in Goldenberg, U.S. Pat. No. 4,624,846, the disclosure of which is incorporated herein in its entirety by reference. The term "localization ratio" is utilized in its conventional sense, i.e. the ratio of target to nontarget antibody conjugate. In general, the second antibody is used in an amount that will enhance the localization ratio of the primary antibody-agent conjugate by at least about 20 percent and typically by 50 percent or more.

The second antibody may be whole IgG or IgM, or a fragment of IgG or IgM, so long as it is capable of binding the primary antibody conjugate to form a complex which is cleared from the circulation and the non-target spaces more rapidly than the primary antibody conjugate by itself. Preferably, the second antibody will be whole IgG or IgM. If the primary antibody is a fragment of IgG or IgM, it is preferable that the second antibody be whole IgG or IgM so that the primary/secondary complex retains the capability of activating the complement cascade. Conversely, where the primary antibody is whole IgG, the second antibody may be a fragment if the complex still retains complement-fixing capability. It is preferred that at least one of the primary/secondary pair be whole IgG or IgM. One advantage of using IgM is that it forms a higher molecular weight complex with primary antibody or with detached conjugates, such as chelating agents and the like. This will increase the rate and effectiveness of clearance of non-target primary antibody and/or imaging component especially from blood. The second antibody can be prepared by methods disclosed in the aforementioned Goldenberg '846 patent. Monoclonal anti-species IgG is also available and is advantageously used as second antibody in the present process. Non-metallic conjugates, e.g., radioiodinated linking groups or organic paramagnetic species such as nitroxides, can also be happens to which the second antibody is specific, as can happens designed for such purpose.

The second antibody is injected into the subject after a sufficient time has elapsed following parenteral administration of the primary antibody-agent conjugate to permit maximum uptake thereof at the lesion, typically anywhere from about minutes to about 24 hours following the initial administration, preferably at about 24–48 hours post-administration. If the primary antibody is not administered intravenously, it may be advantageous to administer at least a portion of the second antibody by the same parenteral route. It is advantageous, however, to inject at least a portion of the second antibody intravenously to accelerate clearance of primary antibody which has diffused into the circulatory system. Normally, both the imaging agent conjugate and the second antibody for clearance will be administered intraarterially or intravenously.

The amount of second antibody introduced will generally be that amount which can decrease the circulating primary antibody by 10–85% within about 0.3 to about 24 hours. The ratio of second antibody to primary antibody which will affect the clearance will depend upon the binding properties of the primary and secondary antibody pair. Preliminary screening of patient blood in vitro can be used to provide an initial estimate of the appropriate ratio. The screen will be used to determine the ratio of second antibody to primary antibody required to obtain a precipitin band in, e.g., a gel diffusion test. This indicates the general range of the molar ratio of second antibody to primary antibody, which serves as a measure of the lower limit for the ratio, since in vivo application may require a higher ratio of second antibody to primary antibody than is indicated by such in vitro tests.

In practice, the molar ratio of second antibody to primary antibody will generally be in the range of about 5–50, although the range should not be considered limitative. Molar ratios of second antibody to primary antibody of 15–25, and preferably 20–25, have been found to be advantageous where both the primary and the second antibody are whole IgG.

The use of second antibody to clear circulating labeled primary antibody and enhance the localization ratio of the primary antibody can be further enhanced by utilization of image-enhancing subtraction techniques as disclosed in the foregoing Goldenberg patents as well as the references cited therein. This is an art-recognized technique wherein an indifferent antibody or fragment labeled with a radionuclide capable of independent detection is injected for use to normalize non-target background levels. This antibody has substantially the same kinetics of distribution and metabolism as the primary antibody during the period required for imaging. The injection of such antibodies is preferred over conventional subtraction agents, such as Tc-99m-labeled serum albumin, which are nevertheless suitable for use to enhance image processing by compensating for background. The use of the radiolabeled indifferent antibody as a subtraction agent permits computerized correction for nontarget background radiation from organs which effect clearance of antibodies from the circulatory system. It will be appreciated by those of ordinary skill in the art that the primary monoclonal antibody and the indifferent antibody utilized as a subtraction agent are preferably from the same species or myeloma/hybridoma so that the second antibody will clear the primary monoclonal antibody and the indifferent antibody immunoglobulin from untargeted areas at substantially the same rate. It is further preferred that the second antibody be specific to a constant region of the primary and indifferent immunoglobulin species.

Targeting selectivity of these conjugates will have application in approving the efficiency of drugs acting on thrombi, emboli, atherosclerotic plaque, and other such cardiovascular lesions.

EXAMPLE 1

Multispecific Anti-leukocyte/Anti-myosin Conjugate

A bispecific F(ab')$_2$ antibody fragment composite is prepared from an Fab' fragment of a monoclonal antibody highly specific for granulocyte cells and an Fab' fragment of a monoclonal antibody specific for cardiac myosin. The interchain disulfide bridges are reduced carefully with cysteine, taking care to avoid light-heavy chain cleavage, to form Fab'-SH fragments. The SH group(s) of the one antibody is(are) activated with an excess of bis-maleimide linker (1,1'-(methylenedi-1,4-phenylene) bismaleimide, Aldrich Chemical Co., Milwaukee, Wis.). The second monoclonal antibody is also converted to Fab'-SH and then reacted with the activated first antibody fragment to obtain a bispecific composite. The composite can be reacted with 2-iminothiolane to introduce one or more sulfhydryl groups for use in coupling the composite to a third antibody/fragment, using the same bis-maleimide activation procedure described above, or for use in direct metallation with, e.g., Tc-99m from reduced (e.g., with $SnCl_2$) pertechnetate. The third antibody of the composite can have the same antigen specificity as one of the other two, or an entirely different specificity such as to monocytes. This composite, conjugated with Tc-99m or one of the other several radionuclides useful for imaging (e.g., those within a range of 100 to 500 keV), is useful for imaging myocardial infarcts of early and late stages.

EXAMPLE 2

Antibody Mixture (Cocktail)

The same antibodies used in Example 1 can be administered as mixtures of antibody fragments or subfragments for the improved imaging of early and late myocardial infarcts.

In this example, anti-myosin antibody (as described by Khaw et al., *Circulation* 57: 743–750, 1978; Khaw et al., *J. Clin. Invest.* 58: 439–446, 1976; Khaw et al., *Hybridoma* 3: 11–23, 1984), preferably the monoclonal antibody R11D10 Fab' of Khaw et al. (*Hybridoma* 3: 11–23, 1984), is mixed with an anti-granulocyte antibody Fab' and the fragments are labeled with Tc-99m for parenteral administration. The mixture achieves comparable results to the composite of Example 1.

EXAMPLE 3

Cardiovascular Imaging Antibody

An anti-leukocyte antibody, preferably an anti-granulocyte antibody imaging agent, is prepared from a monoclonal antibody with selectivity for human granulocytes, such as an NCA-crossreactive antibody. The antibody anti-CEA is converted to Fab'-SH fragments and combined with stannous ions, as described in U.S. patent application 07/408,241, in order to allow for almost instantaneous labeling with Tc-99m from reduced pertechetate. This single antibody preparation is used for imaging a number of cardiovascular lesions, such as atherosclerotic plaques, thrombi and emboli.

EXAMPLE 4

Scintigraphic Imaging Kit

A diagnostic imaging kit contains: a first sterile vial fitted with a rubber septum, and containing the thiol-activated antibody(ies) of Examples 1, 2, or 3, and stannous ions in the form of a lyophilized preparation and additional septum-sealed sterile vials and sterile syringes for labeling and injection of the preparation.

EXAMPLE 5

Diagnostic Imaging of Myocardial Infarction

A 67 year-old male with a history of recurrent angina is admitted to the emergency room complaining of severe chest pain and in a disoriented state. The onset of chest pain is stated to be about 40 minutes earlier. The patient is injected intravenously with 0.25 mg (15 mCi of Tc-99m) of the preparation in Example 3, and the patient's hear scanned by single-photon emission computed tomography (SPECT) 30 minutes and again 2 hours later. Both scanning sessions reveal uptake of Tc-99m in the apical region of the left ventricle, with increased reading confidence from the 2-hour scan, although the lesion is already detectable earlier. Subsequent EKG changes suggest an early infarct, although the atypical features do not permit a conclusive diagnosis. Later studies with thallium indicate a defect in the same area of the heart, confirming the very early detection made by the anti-granulocyte antibody preparation. Later EKG's also show definitive wave abnormalities consistent with the imaging findings.

EXAMPLE 6

Diagnostic Imaging of Deep Vein Thrombosis

An 82-year old woman presents with edema and erythema in her right calf, and is immediately given heparin therapy. A composite mixture of an antigranulocyte antibody Fab', an anti-fibrin antibody Fab', and fibrin Fragment $E_1$ (each at a dose of 0.2 mg and labeled with a total of 20 mCi Tc-99m) are injected intravenously in the left arm. Planar images taken 30 minutes later clearly demonstrate accretion of radioactivity in the calf region of the right leg, in the region of the right tibial vein. No increase of radioactivity is seen in other regions of the body. A contrast venogram the next day confirms the presence of a deep vein thrombosis limited to the posterior tibial vein. Three days after the original antibody-imaging study, the same antibody mixture is administered, and identical imaging findings are obtained, indicating that both early and late thrombosis imaging are feasible.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for detecting and imaging atherosclerotic plaque in the absence of inflammation, which comprises insecting a mammal intravenously or intraarterially with an effective amount for detecting and imaging of a monospecific conjugate comprising an imaging agent conjugated to an antibody or antibody fragment which binds specifically to a monocyte, and obtaining an image of atherosclerotic plaque after sufficient time for said conjugate to bind to said plaque and for unbound conjugate to clear.

2. The method of claim 1, wherein said antibody or antibody fragment is a monoclonal antibody or fragment thereof.

3. The method of claim 2, wherein said antibody fragment is selected from the group consisting of $F(ab')_2$, Fab', Fab, Fv and single chain antibody fragment.

4. The method of claim 1, wherein said imaging agent is a radioisotope emitting gamma radiation in the range of 50–500 KeV.

5. The method of claim 4, wherein said radioisotope is Tc-99m.

6. The method of claim 1, wherein an effective amount for scavenging of a non-labeled second antibody that binds to said conjugate, is injected into said mammal after sufficient time to permit maximum uptake of said conjugate, to enhance clearance of unbound conjugate.

7. The method of claim 6, wherein said effective amount for scavenging is sufficient to reduce the amount of circulating conjugate by 10–85% within about 0.3 to about 24 hours.

8. The method of claim 6, wherein the molar ratio of second antibody to conjugate is about 5–50.

* * * * *